(12) United States Patent
Niazi

(10) Patent No.: US 6,495,174 B1
(45) Date of Patent: Dec. 17, 2002

(54) HERBAL COMPOSITION FOR THE TREATMENT OF ALOPECIA

(76) Inventor: Sarfaraz K. Niazi, 20 Riverside Dr., Deerfield, IL (US) 60015

( * ) Notice: Subject to any disclaimer, the term of this patent is extended or adjusted under 35 U.S.C. 154(b) by 58 days.

(21) Appl. No.: 09/681,204

(22) Filed: Feb. 21, 2001

(51) Int. Cl.$^7$ .......................... A61K 35/78; A61K 65/00
(52) U.S. Cl. ...................... 424/756; 424/725; 424/773; 424/777; 424/778
(58) Field of Search ................................. 424/756, 725, 424/773, 777, 778

(56) References Cited

U.S. PATENT DOCUMENTS 6,159,475 A  *  12/2000  Olguin
6,183,749 B1  *  2/2001  Park
6,339,154 B1  *  1/2002  Kobayashi et al.

FOREIGN PATENT DOCUMENTS

| EP | 319058 | * | 6/1989 |
| JP | DW 1999-497057 | * | 8/1999 |
| KR | DW 2001-429969 | * | 1/2001 |
| KR | DW 2001-472866 | * | 2/2001 |

* cited by examiner

*Primary Examiner*—Christopher R. Tate
*Assistant Examiner*—Randall Winston
(74) *Attorney, Agent, or Firm*—Sarfaraz K. Niazi

(57) ABSTRACT

Described here a composition comprising of alcoholic extracts of herbs RHIZOMA ZINGIBERIS RECENS, RHIZOMA PINELLIAE, FLOS CARTHAMI, RADIX REHMANNIAE, RADIX ANGELICAE SINESIS, RADIX PAENOIAE RUBRA, CACUMEN BIOTAE, SEMEN SESAMI NIGRUM, RADIX POLYGONI MULTIFLORI, FRUCTUS MORI combined with TINCTURE CAPSICUM, TINCTURE CANTHARIDINATE, and OLEUM RICINI for direct application to scalp for the treatment of all kinds of alopecia in humans. Alternately, the herbs listed here can be used individually.

1 Claim, No Drawings

HERBAL COMPOSITION FOR THE TREATMENT OF ALOPECIA

DETAILED DESCRIPTION

Human hair is the keratin-containing threadlike outgrowth extending from hair follicles in the skin. In humans, hair generally serves protective, sensory, and sexual attractiveness functions. A mature hair shaft is composed of three, and sometimes four, basic structures. The cuticle is the thick outer protective covering consisting of flat overlapping scale-like layers. The cortex is located inside, and is surrounded by, the cuticle. The cortex contains fibrous proteins, which are aligned along the length of the hair axis. Thicker hairs often contain one or more porous regions, the medulla, located near or at the center of the hair shaft. The fourth basic component is the intercellular cement, which glues or binds the cells together and provides the main pathway for diffusion into the hair fibers. Melanocytes, which produce melanin, the pigment responsible for hair color, are generally contained in the cortex and the base of the bulb of the hair shaft. Essential nutrients and oxygen are carried to the growing hair through capillaries around the base of the bulb. The hair follicle cycle is a complex process and entails involvement of cell differentiation, epithelial-mesenchymal interactions, stem cell augmentation, pattern formation, apoptosis, cell and organ growth cycles, and pigmentation. The most important theme in studying the cycling of hair follicle is that the follicle is a regenerating system. By traversing the phases of the cycle (growth, regression, resting, shedding, then growth again), the follicle demonstrates the unusual ability to completely regenerate itself. The basis for this regeneration rests in the unique follicular epithelial and mesenchymal components and their interactions. Recently, some of the molecular signals making up these interactions have been defined. They involve gene families also found in other regenerating systems such as fibroblast growth factor, transforming growth factor-β, Wnt pathway, Sonic hedgehog, neurotrophins, and homeobox. (K S Stenn and R Pauls, Physiol Rev 2001 Jan; 81(1):449–494).

Normal hair follicles cycle between a growth stage (anagen), a degenerative stage (catagen), and a resting stage (telogen). The scalp hairs have a relatively long life cycle: the anagen stage ranges from two to five years, the catagen stage ranges from a few days to a few weeks, and the telogen stage is approximately three months (Fitzpatrick, T. B., et al., eds., DERMATOLOGY IN GENERAL MEDICINE (Vol. I), McGraw-Hill, Inc., 1993, pp. 290–291; Sperling, L. C., J. Amer. Acad. Dermatology (v. 25, No. 1, Part 1), pp. 1–17 (1991)). Shorter hairs found elsewhere on the body have corresponding shorter anagen duration. The morphology of the hair and the hair follicle changes dramatically over the course of the life cycle of the hair. During anagen, the hair follicle is highly active metabolically (Sperling, L. C., J. Amer. Acad. Dermatology (v. 25, No. 1, Part 1), p. 4 (1991)). The follicle comprises a follicular (dermal) papilla at the base of the follicle; epidermal matrix cells surrounding the follicular papilla and forming the base of a hair shaft; and the hair shaft that extends upwards from the papilla through the hair canal (Fitzpatrick, T. B., et al., eds., DERMATOLOGY IN GENERAL MEDICINE (Vol. I), McGraw-Hill, Inc., 1993). The matrix cells are the actively growing portions of the hair (Sperling, L. C., J. Amer. Acad. Dermatology (v. 25, No. 1, Part 1), p.6 (1991)). At catagen, the matrix cells retract from the papilla, and other degenerative changes occur (Sperling, L. C., J. Amer. Acad. Dermatology (v. 25, No. 1, Part 1), pp. 13–14 (1991)). A column of epithelial cells pushes the keratinized proximal shaft of the hair upwards (Sperling, L. C., J. Amer. Acad. Dermatology (v. 25, No. 1, Part 1), p. 3 (1991)), and cell death occurs within the follicle (Fitzpatrick, T. B., et al., eds., DERMATOLOGY IN GENERAL MEDICINE (Vol. I), McGraw-Hill, Inc., 1993, p. 291). When the hair follicle reaches the telogen stage, the existing hair has a club-shaped proximal end, and a small bud (a remnant of the epithelial column that is found in catagen) at the base of the follicle (Sperling, L. C., J. Amer. Acad. Dermatology (v. 25, No. 1, Part 1), p. 3 (1991)). A telogen hair will not grow further (Fitzpatrick, T. B., et al., eds., DERMATOLOGY IN GENERAL MEDICINE (Vol. I), McGraw-Hill, Inc., 1993, p. 291). The pigmentary system that colors hair involves melanocytes located in the matrix area of the follicle, above the follicular papilla (Fitzpatrick, T. B., et al., eds., DERMATOLOGY IN GENERAL MEDICINE (Vol. I), McGraw-Hill, Inc., 1993, p. 292). Melanin pigments produced by the melanocytes flow along dendritic processes (Fitzpatrick, T. B., et al., eds., DERMATOLOGY IN GENERAL MEDICINE (Vol. I), McGraw-Hill, Inc., 1993, p. 292). The dendritic processes are phagocytized by the differentiating matrix cells that become part of the hair shaft; degradation of the phagocytosed material results in release of melanin granules into the cytoplasm (Fitzpatrick, T. B., et al., eds., DERMATOLOGY IN GENERAL MEDICINE (Vol. I), McGraw-Hill, Inc., 1993, p. 671), thus pigmenting the hair. Alterations in normal hair pigmentation or growth may be caused by age, physiologic disease conditions, or injury especially, for example, exposure to ultraviolet-irradiation. The "graying" of hair, both normal (age-associated) and abnormal, is known as canities. Graying results from a progressive decrease in pigment present in the hair shaft, caused by loss of melanocytes (Fitzpatrick, T. B., et al., eds., DERMATOLOGY IN GENERAL MEDICINE (Vol. I), McGraw-Hill, Inc., 1993, p. 671; Gilchrest, B. A., SKIN AND AGING PROCESSES, CRC Press, 1984, p.19). A decrease in the density of hair follicles is also associated with advancing age (Gilchrest, B. A., SKIN AND AGING PROCESSES, CRC Press, 1984, p. 20). Alopecia areata is a common disease of the hair follicle, affecting about 2% of new patients attending dermatology clinics in the United States and in Britain (Price, V. H., J. Invest. Dermatol., 96:685 (1991)). In alopecia areata, the hair follicle, in response to some unknown signal or injury, is suddenly precipitated into premature telogen, and then cycles in a shortened aborted cycle in which it is repeatedly arrested part way through early anagen. The follicle may remain in this arrested state but is capable of resuming normal growth after months or years. The nature of the signal or injury and the anatomical target for this abnormality are unknown. Histologically, alopecia areata is characterized by peribulbar lymphocytic infiltrate of predominantly T helper cells (Lever, W. F. and Schaumburg-Lever, G., eds., HISTOPATHOLOGY OF THE SKIN, J. B. Lippincott Co., Philadelphia, Pa., 1990, pp. 223–224), strongly suggesting the involvement of the cellular immune system perhaps through a loss of discrimination of self and non-self antigens (Goldsmith, L. A., J. Invest. Dermatol., 96:985–1005 (1991)). Alternatively, an intrinsic abnormality in the follicular keratinocyte could be activated under the influence of internal or external triggers, which eventually may lead to cellular degeneration and peribulbar inflammatory infiltrate. However, to date no specific antigen has been identified to support the autoimmune theory and no specific intrinsic difference has been reported between normal bulbar and alopecia areata keratinocytes. The hair follicle is an epidermal derivative that undergoes cycles of growth, involution, and rest. The hair cycle has well-orchestrated kinetics regulated by interactions between mesenchymal and epithelial cells, although the intracellular signals remain unclear. There is suggestion that telogen-to-anagen progression required organized keratinocyte migration in response to mesenchymal stimuli.

Alopecia (baldness) a deficiency of hair, either normal or abnormal, is primarily a cosmetic problem in humans. Hair loss occurs in a variety of situations. These situations include male pattern alopecia, alopecia senilis, alopecia areata, diseases accompanied by basic skin lesions or tumors, and systematic disorders such as nutritional disorder and internal secretion disorders. The mechanisms causing hair loss are very complicated, but in some instances can be attributed to aging, genetic disposition, the activation of male hormones, the loss of blood supply to hair follicles, and scalp abnormalities. It is a deficiency of terminal hair, the broad diameter, colored hair that is readily seen. However, in the so-called bald person although there is a noticeable absence of terminal hair the skin does contain vellus hair, which is a fine colorless hair, which may require microscopic examination to determine its presence. This vellus hair is a precursor to terminal hair. In both women and men, the occurrence of an increased loss of hair is accompanied by the fear of becoming totally bald-headed. Besides the medical aspect, disturbances in the hair growth thus present a great personal problem for the affected person. The rate of growth of the hair amounts to about 0.35 mm per day, the hair density is from about 80,000 to 150,000 hairs per head. A loss of 100 hairs per day constitutes already a pathological effluvium. From hair follicles that remained intact, hair is able to re-grow. However, during a multiphase, lengthy re-growth, hair follicles may shrink and lead to a gradual loss of hair.

The existence of a number of pathologic syndromes depends on androgen hormones. An unexplained switch causes androgenic alopecia from the growth promoting effect of androgens on the hair follicles to hair loss. In skin, androgen mediated disorders, such as alopecia, acne vulgaris, and hirsutism, excess of the cutaneous androgens are a major nosological factor. The androgenic hormones can act only via an androgenic receptor, which is a transcription factor, a protein that interacts with a specific region of DNA. Thus, the mode of action of testosterone and its much more potent analog, 5-alpha dihydrotestoterone depends upon binding to the androgenic receptors. Only then can transcription by RNA polymerase 11 take place. In the treatment of androgenic alopecia, various antiandrogens originally developed for the treatment of prostate cancer were claimed for systemic use, but side effects of chronic therapy with these systemically absorbable substances were of concern. The U.S. Pat. No. 6,184,249 to Sovak, et al., is for the use of substituted phenylalanines that bind specifically to androgen receptor reducing the incidence of alopecia. The U.S. Pat. No. 6,174,892 to Gormley, et al., is for a method of treating and/or reversing androgenic alopecia and promoting hair growth, and methods of treating acne vulgaris, seborrhea, and female hirsutism, by administering to a patient in need of such treatment a 5-α-reductase 2 inhibitor, such as finasteride.

One form of hair loss, alopecia areata, is known to be associated with autoimmune activities; hence, topically administered immunomodulatory compounds demonstrate efficacy for treating that type of hair loss. The immunosuppressant drugs FK506, rapamycin and cyclosporin are well known as potent T-cell specific immunosuppressants, and are effective against graft rejection after organ transplantation. Topical application of FK506 (Yamamoto et al., J. Invest. Dermatol., 1994,102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189, 042; and Ok et al., U.S. Pat. No. 5,208,241; Rupprecht et al., U.S. Pat. No. 5,284,840; Organ et al., U.S. Pat. No. 5,284, 877). Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth. Honbo et al., in EP 0 423 714 A2 disclose the use of relatively large tricyclic compounds, known for their immunosuppressive effects, as hair revitalizing agents.To overcome the side effects of immunosuppressants, several developments have been made using nonimmunosuppressant techniques. Hamilton and Steiner disclose in U.S. Pat. No. 5,614,547 a novel pyrrolidine carboxylate compounds, which bind to the immunophilin FKBP12 and stimulate nerve growth, but which lack immunosuppressive effects. The U.S. Pat. No. 6,177,455 to Steiner, et al., is for pharmaceutical compositions and methods for treating alopecia and promoting hair growth using non-immunosuppressant pyrrolidine derivatives.

Stem cells are by definition present in all self-renewing tissues. These cells are believed to be long-lived, have a great potential for cell division and are ultimately responsible for the homeostasis of steady-state tissues. Stem cells are normally slow cycling. They can, however, be induced to enter the proliferative pool in response to certain growth stimuli. When stem cells undergo occasional cell division, they give rise to more rapidly proliferating "transient amplifying cells" ("TA"). Stem cells possess many of the following properties: they are relatively undifferentiated, ultrastructurally and biochemically; they have a large proliferative potential and are responsible for the long term maintenance and regeneration of the tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell, and they are usually found in well protected, highly vascularized and innervated areas. Positive identification of stem cells has been difficult because, there are few known immunological or biochemical markers specific for epithelial stem cells. Since they are normally "slow-cycling", they cannot be labeled by single pulse administration of radioactive materials typically used to detect actively proliferating TA cells. The U.S. Pat. No. 5,756,094 to Lavker, et al., describes a method for identification of these cells by labeling these cells continuously to generate label-retaining cells (LRCs). Cotsarelis et al., J. Invest. Dermol. 1989a, 92(3) disclose a method to facilitate detection of LRCs based on the ability of slow-cycling cells to be recruited to proliferate in response to hyperplastic stimuli.

Stem cells of various epithelia share a common set of features. It is shown that in hair follicles, the heavily pigmented stem cells are located at the base, in close proximity with follicular papillae and associated vasculature. Cotsarelis, et al., Cell 1990, 61: 1329–37, show that the hair follicle stem cells were found to exist exclusively in the mid-portion of the follicle at the arrector pili muscle attachment site termed the "bulge" area of the hair follicle.

A number of growth factors have been reported to be useful for modulating stem cell activity. For example, cytokines such as Tumor Necrosis Factor (TNF), Epidermal Growth Factor (EGF), Transforming Growth Factor (TGF) and Interleukin-(IL-1) are believed to be useful. Cellular targets in acute graft versus host disease have been postulated to be keratinocytes with stem cell properties. Because stem cells are normally slow cycling but proliferate rapidly upon inductive stimulation, they may be attractive targets for cytokines such as TNF. EGF has been shown to have broad biological effects. Most significantly, it has the ability to induce the proliferation of basal keratinocytes. Furthermore, it has been shown to support growth during fetal development and accelerate re-epithelialization during wound healing. TGF-α has been shown to be involved in the regulation of both growth and differentiation of epithelial cells. It is known to stimulate keratinocyte growth in vitro. IL-1 is known to induce proliferative activity in epidermal cells. Keratinocytes of the basal layer of the epidermis express the high affinity (trk E and trk) and the low affinity (p75) NGF receptors (NGF-R). NGF, produced by keratinocytes, protects cells from death when it binds to NGF receptors. In cells, this NGF effect is mediated in part by induction of the protective protein Bcl-2. Interestingly, basal epidermal keratinocytes express Bcl-2 protein. Normal anagen hair follicles strongly express the p75 NGF-R and that p75 NGF-R expression is significantly reduced and limited to a few basal keratinocytes in telogen hair follicles. The U.S. Pat. No. 6,103,689 to Gilchrest, et al., is for a method for maintaining hair growth and coloration in humans by using neurotrophin ligands to prevent p75 nerve growth factor (NGF) receptor mediated apoptosis in melanocytes and keratinocytes.

Several novel techniques and preparations have been described to promote hair growth based on the various theories and techniques described above. The U.S. Pat. No. 5,607,693 to Bonte, et al., is for a cosmetic or pharmaceutical composition which comprises oxyacanthine or an extract of a plant in which it is present, such as Berberis vulgaris or barberry. One particular association is that of oxyacanthine with a saponin. This composition can be intended in particular for stimulating hair growth, retarding hair loss or combating pruritus. The U.S. Pat. No. 6,159,475 to Olguin for a hair growth formulation. The two basic main ingredients are castor oil and a special lemon extract. The U.S. Pat. No. 6,149,933 to Nelson is for a dietary supplement, which is useful for the promotion of healthy hair, and pigment restoration in human subjects is provided. The dietary supplement contains a copper salt, p-aminobenzoic acid, pantothenic acid and vitamin B6. The U.S. Pat. No. 6,013,279 to Klett-Loch is for a combination preparation for stimulating the growth of hair and skin and nails with a combination of vitamins, enzymes, and amino acids. To increase the effectiveness of the combination preparation, its use is described as a supplement to a topically applicable hair growth stimulant, in particular a thymus-containing therapeutic agent. The U.S. Pat. No. 5,972,345 to Chizick, et al., is for a natural formulation for treatment of male pattern hair loss. The formulation contains a combination of Saw Palmetto extract, African Pygeum extract, stinging nettle extract, and optionally zinc, vitamin B6 and green tea extract. The U.S. Pat. No. 6,183,749 to Park is for a dietary supplement containing herbal extracts, which promote healthy hair growth on the scalp. A composition of a dietary supplement comprising MAMMALIA PLACENTA prepared from the placenta of a mammal, FRUCTUS LIGUSTRI LUCIDI, SALVIAE MILTIORRHIZAE, PAEONIAE RUBRA, CINNAMOMI CASSIAE, MOUTAN RADICIS, and ALISMATIS PLANTAGO-AQUATICA. For increased benefit, the dietary supplement further comprising POLYGONI MULTIFLORI, FRUCTUS LYCII CHINENSIS, FRUCTUS MORI ALBAE, VACCARIAE SEGETALIS, PLATICODI GRANDIFLORI, COICIS LACHRYMA-JOBI, and ARTEMESIAE CAPILLARIS. The dietary supplement is for oral ingestion and can be prepared in the form of a tablet, capsule, powder or syrup. The U.S, Pat. No. 5,738,879 to Rine is for scalp hair treatment method and composition wherein the composition comprises deionized water, a vasodilator (such as ethyl nicotinate and/or capsicum extract), a magnesium salt, and a hydrolyzed protein. Other patents that promote multiple use of herbal extracts include the U.S. Pat. No. 5,869,059 issued to Garza teaches an herbal composition beneficial for the treatment of hemorrhoid and the U.S. Pat. No. 5,770,207 issued to Bewicke, which teaches a dietary supplement containing herbal extracts that, serves as a general relaxant. The U.S. Pat. No. 5,738,879 to Rine is for a scalp and hair treatment method and composition wherein the composition comprises deionized water, a vasodilator (such as ethyl nicotinate and/or capsicum extract), a magnesium salt, and a hydrolyzed protein.

In the present invention, a variety of herbs or their herbal extracts in specific compositions are described that promote hair growth to treat the condition of alopecia. The herbs found useful in promoting hair growth include: RHIZOMA ZINGIBERIS RECENS, RHIZOMA PINELLIAE, FLOS CARTHAMI, RADIX REHMANNIAE, RADIX ANGELICAE SINESIS, RADIX PAENOIAE RUBRA, CACUMEN BIOTAE, SEMEN SESAMI NIGRUM, RADIX POLYGONI MULTIFLORI, FRUCTUS MORI, TINCTURE CAPSICUM, TINCTURE CANTHARIDINATE, OLEUM RICINI, [Note: The pharmaceutical terms used have the following meaning: SEMEN (seed), CORTEX (stem cortex), RHIZOMA (rhizome or root), RADIX (root) FRUCTUS (fruit) portion, OLEUM (oil).] This composition acts by multiple mechanisms including but not limited to: enhancing nutrition of follicular cells, enhanced blood flow to follicles, stimulation of stem cells to create new follicles. In a preferred embodiment, alcoholic extracts are made of all herbs listed above are made in tinctures listed above along with ethanol, mixed with other ingredients and and applied 2–3 times a day to balding areas of scalp for a period of 2–3 months.

Several of these herbs have been a topic of patented products. The U.S. Pat. No. 5,916,555 to Lee, et al., is for a pharmaceutical composition for the treatment of diabetes. More specifically, the present invention relates to a composition containing 17 kinds of main natural drugs, i. e. Cordyceps, Bezoar bovis, Carthami flos, Astragali radix, Hirudo, Polygoni cuspidati radix, Polygonati falcati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix and Rehmaniae radix crudae. In addition to 17 kinds of main natural drugs, if desired, the composition of the present invention can contain one or more supplementary natural drugs selected from the group consisting of Liriopsis tuber, Cistanchis herba, Adenophorae radix, Salviae radix, Ginseng radix rubra, Anemarrhenae rhizoma, Pachymae fungus, Phellodendri cortex, Mori radicis cortex, Schizandrae fructus, Galli stomachichum corium, Trichosanthis radix, Rhei rhizoma, Dioscoreae rhizoma, Alisma rhizoma, Polygoni multiflori radix, Galla rhois, Formica fusca L., Sanchi ginseng, Margaritum. The U.S. Pat. No. 5,622,704 to Hacker, et al., is for a herbal anxiolytic composition containing Rhizoma zingiberis and Ginkgo bilobae. The U.S. Pat. No. to Kim 5,225,203 is for a pharmaceutical liquid composition containing Bezoar bovis, Dioscoreae rhizoma, Glycyrrhizae radix, Ginseng radix, Typhae Pollen, Massa medicata fermentata, Sojae germinatum Semen, Cinnamomi cortex, Gelatin, Paeoniae radix liriopis Tuber, Scutellariae radix, Angelicae gigantis radix, Ledebouriellae radix, Atractylodis rhizoma alba, Bupleuri radix, Platycodi radix, Armeniacae Semen, Hoelen, Cnidii rhizoma, Antellopis cornu, Moschus, Borneol, Ampelopsis radix, and Zingiberis rhizoma for easy oral and parental administration thereof to critical patients. The U.S. Pat. No. 4,618,495 to Okuda, et al., is for a composition for reducing cancer symptoms by improving lipid metabolism and eliminating or reducing anorexia in tumor-bearing patients through inhibition of the lipid degradation-promoting action of toxohormone L which comprises an aqueous or aqueous organic solvent extract of one or more crude preparations selected from the group consisting of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix. The U.S. Pat. No. 4,61 3,591 to Aburada, et al., is for a herbal composition, an adminiculum increasing the antitumor activities of mitomycin C and doxorubicin hydrochloride and decreasing the side effects associated with their use comprising an aqueous or aqueous organic solvent extract of a crude preparation of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix. The U.S. Pat. No. 5,587,167 is for a pharmaceutical composition for prophylaxis and treatment of premature ejaculation containing the alcohol and/or aqueous extracts of ginseng radix, angelicae gigantis radix, broomrape, cassiae cortex, asiasari radix and bufonis venenum as the essential galenic components and, if necessary, one or more additional components selected from the extracts of xanthoxyli fructus, cnidium fructus, caryophylli flos and moschus. The U.S. Pat. No. 5,466,443 Ho, et al., is for a herbal-based oral composition for promoting darkening of human hair color upon periodic retention of the composition within the oral cavity includes an herbal mixture included at a level of from 2.5 to 15% of the total weight of the herbal mixture in a toothpaste or chewing gum base. The herbal mixture includes prepared Rhizoma Ligustici Chuanxiong, Calculus Bovis, Indigo Naturalis, Herba Ecliptae, Radix Polygoni Multiflori, Pericarpium Trichosanthis, Radix Sophorae Flavescentis, Spina Gleditsiae, Radix Angelicae Sinensis, Rhizoma Drynariae, Fructus Mori, and Halitum. The U.S. Pat. No. 6,074,608 to Lee is for a composition and method for narcotics withdrawal containing Amanae bulbus, Puchrestrae radix, Euphorbiae pekinensis, Lathyridis semen, Auicular margark feral, Manis squama, Zizyphi spinosi semen, Angelicae gigantis radix, Cnidii rhizoma, Rehmaniae radix and Paeoniae radix. The U.S. Pat. No. 4,618,495 to Okuda, et al., is for a composition for reducing cancer symptoms by improving lipid metabolism and eliminating or reducing anorexia in tumor-bearing patients through inhibition of the lipid degradation-promoting action of toxohormone L which comprises an aqueous or aqueous organic solvent extract of one or more crude preparations selected from the group consisting of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix. The U.S. Pat. No. 6,074,648 to Lee is for a preparation for prevention and treatment of hepatocarcinoma containing 4 kinds of main natural drugs, i.e., Hedyotidis herba, Curcumae longae rhizoma, Polygonati cuspidati radix and Sophorae tonkinesis radix; and an oral composition having a preventive and therapeutic effect against fatty liver and hepatic cirrhosis and containing 10 kinds of natural drugs, i.e., Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma and Acori graminei rhizoma, and which can effectively prevent the development of hepatic diseases including hepatitis, fatty liver and hepatic cirrhosis into hepatocarcinoma and treat hepatocarcinoma by combined administration of two kinds of the compositions.

Since the purpose of this invention is to achieve substantial penetration of the constituents of the composition, the composition includes optionally, an absorption promoter which may include a substantially water-insoluble transdermal penetration enhancing compound selected from the group consisting of C4 to C16 aliphatic group substituted acetals, hemi-acetals and morpholines and further comprising a physiologically acceptable water soluble polar compound selected from the group consisting of alcohols, glycols, lactams, urea, cycloethylene urea, 1,3-dioxolone, 2-methyl-1-3-dioxolone, 1,3-dioxane, 2 methyl-1,3-dioxane, morpholine, N-methylmorpholine, N-dimethylformamide, dimethylsulfoxide, methylacetate, ethyllactate, monosaccharides, polysaccharides, amino acids, amino alcohols, diethylamine and cycloethylene carbonate. The polar compound may be selected from a group consisting of alcohol, glycol, dioxolane, formamide, carbonate, glucose, urea and mixtures thereof. Alternatively, the polar compound may be an alcohol glycol mixture or lactim. Other compounds include 1-dodecylazacycloheptan-2-one hexamethylene-lauramide, N-methyl-2-pyrrolidone, a sucrose aliphatic acid ester, and nonionic surfactants, in an amount of 0.5–25% by weight of the preparation.

For topical administration, it is preferred that the growth-stimulating composition be formulated in an alcoholic or hydro-alcoholic solution that in itself acts to dissolve or remove sebaceous secretions, which may interfere in the absorption of the active ingredients. The type of formulation and amount of the formulation applied will be determined to a large extent by the caregiver. While a single application of the composition may be effective, in order to obtain the best results it may be necessary to apply it periodically, such as every day, or every other day depending upon the individual and the state of the cells being treated. Again the amount of the composition and the frequency at which it is applied, is a matter which can readily be determined by one skilled in the art based upon visual changes observed in hair growth.

A typical composition of the preferred embodiment is given below. The composition is prepared by extracting powdered herbs in the mixture of tinctures and extra alcohol for a period of two weeks in a sealed stainless steel container. The solid parts are removed by compression filtration and the composition brought to volume with alcohol: Flos Carthami 20 G, Rhizoma Zingiberis recens 30 G, Radix Rehmanniae 33 C, Radix Angelicae Sinensis 33 G, Radix Paeonoiae Rubra 33 G, Cacumen Biotae 33 G, Rhizoma Pinelliae 30 G, Semen Sesami Nigrum 15 G, Radix Polygoni Multiflori 10 G, Fructus Mori 5 G, Tincture Cantharidinate (10%) 150 mL, Tincture Capsicum(10%) 150 mL, Oleum Ricini 25 mL, Dimethylsulfoxide 50 mL, Alcohol USP Qs to 1 L.

The direct evidence of effectiveness of the products was demonstrated using animals. The test is based on a study of the activity of the invention on the pilary cycle of Sprague Dawley rats, all of which are 23 days old. The pilary cycles of all the animals are still synchronous at this age. The aim of the test was more particularly to demonstrate the action of the invention on the prolongation of the hair growth phase or so-called "anagenic phase." This is done in the following manner. On day 24, all the rats are shaved on the sides of the lower part of the back so as to leave only a short length of hair, which is just enough to allow subsequent depilation, From day 25 (age of the rats) to day 65, the test products are then applied daily at a dose, which changes with the weight of the animals. This dose is 0.5 ml on day 25 and reaches 2 ml on day 65. At substantially regular intervals of time (about every 3rd day), starting from day 28, a tuft of hairs is removed from the animal's left side using tweezers. The roots of 10 hairs selected at random from this tuft are observed under high magnification and the number of hairs in the anagenic phase, recognizable by the characteristic shape of the root, is counted. The percentage of hairs in the anagenic phase (growth phase) is thus determined as a function of time on groups of 10 animals. The study was performed on 30 rats divided into 3 groups of 10 animals.

The first group receives a preparation according to the invention; the second group received only the excipients. The third group is the control group, which does not receive any product. In all instances the anagenic phase was more prolonged in the rats treated with the invention, in comparison with the rats treated with the excipients only or in the control group. This was particularly marked from day 37 onwards. Thus it was clear that, by extending the duration of the anagenic phase, the invention described here substantially retards hair loss and promotes renewed growth. It was established from these studies that the specific combination of herbs described here significantly enhances growth of hair and thus found useful in the treatment of alopecia. The exact dose and mode of application can vary among individuals and anyone with requisite knowledge about treatment of human ailments should be able to judge and thus recommend an appropriate dosing of these compositions.

What is claimed is:

1. A pharmaceutical composition for the topical treatment of alopecia it in humans and animals, consisting essentially of effective quantities of alcoholic extracts of *Rhizoma zingiberis recens, Rhizoma pinelliae, Flos carthami, Radix rehmanniae, Radix angelicae sinesis, Radix paenoiae rubra, Cacumen biotae, Semen sesami nigrum, Radix polygoni multiflori, Fructus mori, Capsicum, Cantharidin*, and *Oleum ricini* in a pharmaceutical carrier.

* * * * *